US00PP37271P2

(12) United States Plant Patent
Moon

(10) Patent No.: US PP37,271 P2
(45) Date of Patent: Feb. 17, 2026

(54) ***ULMUS* TREE NAMED 'UCMTF'**

(50) Latin Name: *Ulmus crassifolia*
Varietal Denomination: UCMTF

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 19/083,845

(22) Filed: Mar. 19, 2025

(51) Int. Cl.
*A01H 6/00* (2018.01)
*A01H 5/00* (2018.01)

(52) U.S. Cl.
USPC ..... Plt./221

(58) Field of Classification Search
USPC ..... Plt./221
CPC ..... A01H 5/00; A01H 6/00
See application file for complete search history.

*Primary Examiner* — Keith O. Robinson

(57) ABSTRACT

A new and distinct cultivar of *Ulmus crassifolia* tree named 'UCMTF' is disclosed, characterized by distinctive red emerging foliage, turning dark green with maturity. New growth is uniquely greyed-purple. The canopy of the tree is upright and narrow. The new variety is a *Ulmus* tree, typically used for landscapes and gardens.

3 Drawing Sheets

Latin name of the genus and species: *Ulmus crassifolia.*
Variety denomination: 'UCMTF'.

BACKGROUND OF THE INVENTION

The inventor discovered the new cultivar in the Summer of 2019 growing as a seedling in a production field in at a tree farm in Washington, Georgia, among a group of cross-pollinated Cedar Elm. The cross-pollination resulting in the new variety is assumed to have occurred during 20107. Evaluation of this tree has continued on a tree farm located in Washington, Georgia, Wilkes County.

Asexual reproduction by grafting of the new cultivar 'UCMTF' was first performed 16 during the Winter of 2020 at a farm in Washington, Georgia. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that my new Cedar Elm tree as particularly evidenced by the upright growth and red flush. These genetic traits can be consistently reproduced by asexual propagation.

SUMMARY OF THE INVENTION

The cultivar 'UCMTF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'UCMTF' grown in Washington, Georgia. These characteristics in combination distinguish 'UCMTF' as a new and distinct *Ulmus crassifolia* cultivar:

1. Dark green mature foliage.
2. Red emerging foliage.
3. Greyed-purple new growth.
4. Upright, narrow canopy.
5. Fast growth rate.

PARENT COMPARISON

The parent varieties cannot be specifically identified.

COMMERCIAL COMPARISON

Trees of the new cultivar 'UCMTF' are similar to trees of the commercial variety, *Ulmus crassifolia* 'Everalan' U.S. Plant Pat. No. 36,522 in most horticultural characteristics. However, plants of the new cultivar 'UCMTF' differ in the following:

1. The new variety has red emerging foliage not seen in this comparator.
2. The new variety has Greyed-Purple stem and petiole coloration not seen in this comparator.

Plants of the new cultivar 'UCMTF' are similar to trees of the species, *Ulmus crassifolia* found in the nursery trade in most horticultural characteristics. However, plants of the new cultivar 'UCMTF' differ in the following:

1. The new variety has red emerging foliage not seen on the species.
2. The new variety has narrower, and more upright growth than the species.
3. The new variety has a strong central leader not seen in the species.
4. The new variety has Greyed-Purple new growth not seen on the known species.

BRIEF DESCRIPTION OF THE PHOTOGRAPHS

Figure 1:
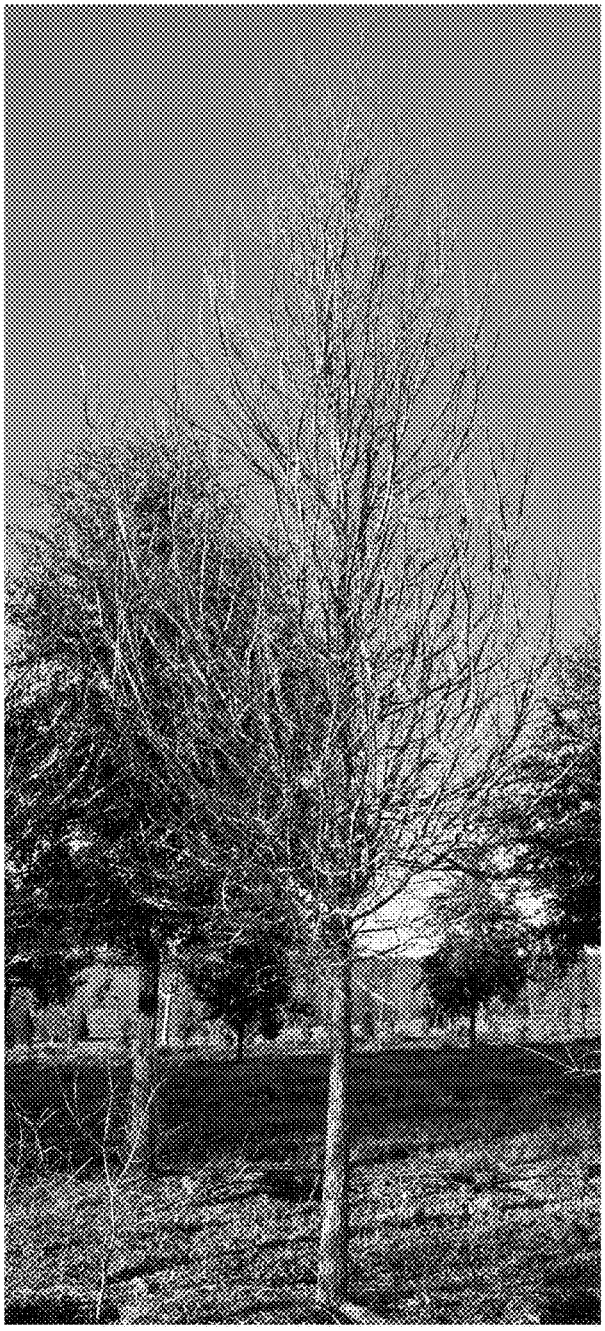

The accompanying photograph in FIG. 1 illustrates a tree of the new variety at about 4 years of age planted in a field. The photograph was taken during winter while the tree has no foliage, allowing the branch structure to be clearly seen.

Figure 2:
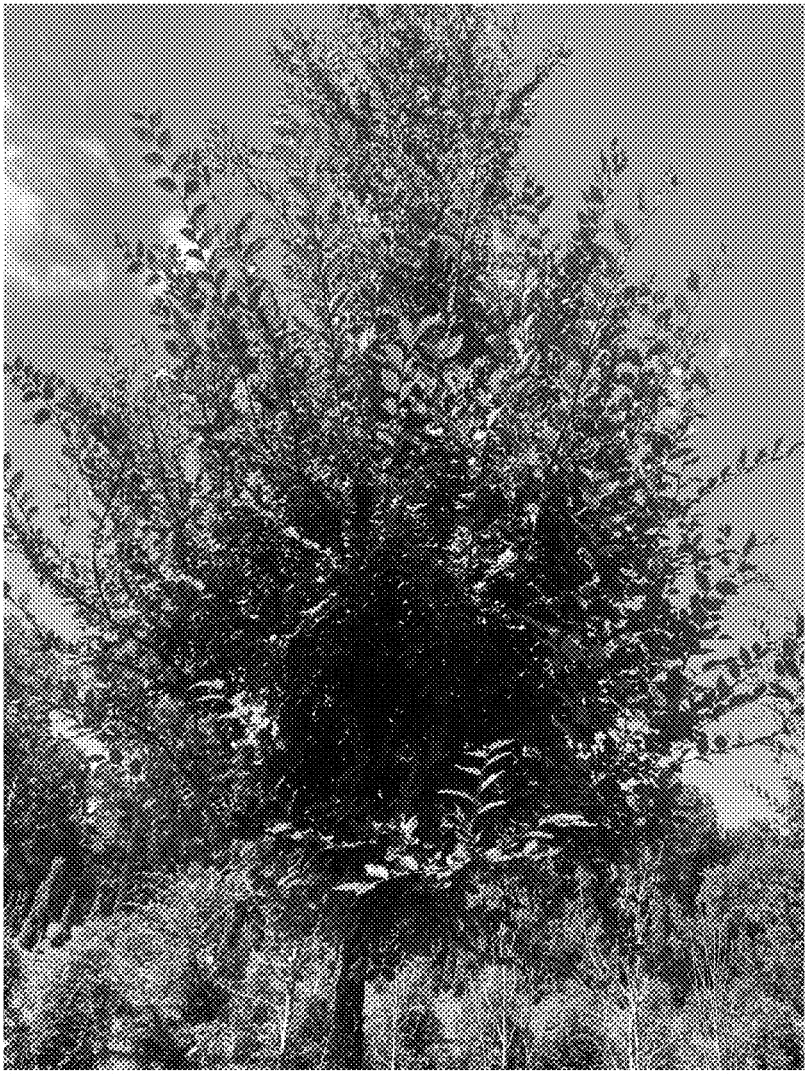

FIG. 2 illustrates emerging young and mature foliage during Spring on a 4-year old tree.

Figure 3:
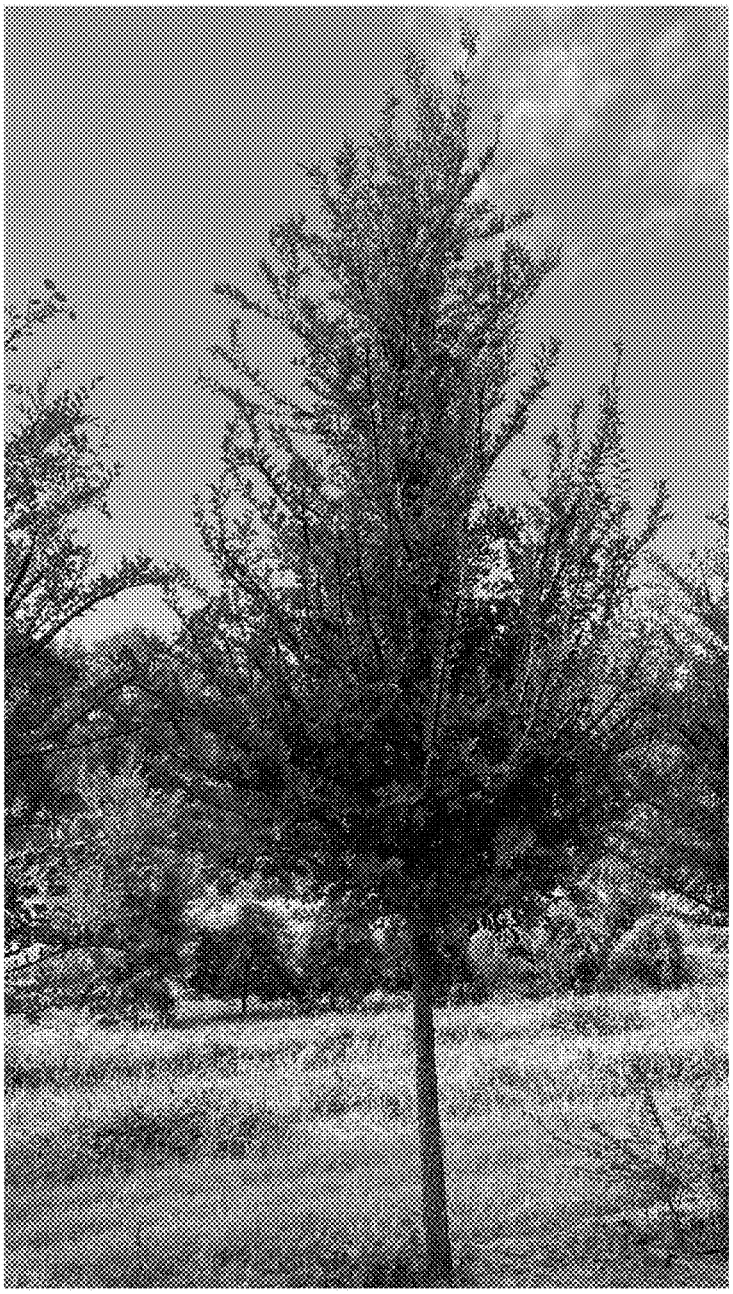

FIG. 3 a tree of about 4-years old during Summer in Washington, GA.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'UCMTF' plants grown outdoors and in a nursery in Washington, Georgia. Plants are approximately 2 years old, in a 3 gallon nursery container. Temperatures ranged from 5° C. to 10° C. at night to 18° C. to 27° C. during the day. Measurements and numerical values represent averages of typical plant types.

Botanical classification: *Ulmus crassifolia* 'UCMTF'.

PROPAGATION

Cleft grafting.

Roots not observed.

TREE

Growth habit: Deciduous pyramidal tree.

Height: Approximately 14 feet at 3 years.

Spread: Approximately 8 feet at 3 years.

Branch/stem color:

*New growth*.—Near RHS Greyed-Purple N187C flushed N186C.

*Mature*.—Near RHS Greyed-Purple N187C flushed 183B.

*Texture*.—Moderately dense lenticels on both new and mature growth. 2 mm long, 1 mm wide. Lenticels colored near White 155A. Mature growth scaly.

Branch shape: Round.

Branch length: Average 4 meters.

Branch width: Average 15 cm.

Aspect and angle: Lower ⅓ branches occur at 45 degrees from center. Upper ⅔ branches occur at 45 degrees or less from center, most commonly about 30 degrees from center.

Growth rate: Rapid.

Trunk characteristics:

*Color*.—Near RHS Greyed-Brown N199A. Bark Greyed-Green 197C and 197D.

*Surface texture*.—Furrowed and scaly.

FOLIAGE

Leaf:

*Arrangement*.—Alternate.

*Shape*.—Ovate.

*Average length*.—Average 3 cm to 4 cm excluding petiole.

*Average width*.—Approximately 2 cm.

*Apex*.—Acute.

*Base*.—Broad tapered or blunt.

*Margin*.—Uniformly serrate. Moderately to densely serrate.

*Attachment*.—Petiolate.

*Aspect*.—Moderately upwardly cupped.

*Quantity*.—About 25 to 40 per 100 linear cm.

*Leaf internode length*.—2.5 to 4 cm.

*Leaf fragrance*.—None detected in Summer.

*Texture of top surface*.—Glabrous.

*Texture of lower surface*.—Glabrous.

*Color*.—Emerging foliage: Upper side: Near RHS Red 42C flushed 42A, turning Greyed-Yellow 162B flushed 42C. Under side: Near RHS Red 42C flushed 42A turning Greyed-Yellow 162B flushed 42C. Young foliage: Upper side: Near RHS Green 143A. Under side: Near RHS Green 143B. Mature foliage: Upper side: Near RHS Green 137A flushed 139A. Under side: Near RHS Green 137D.

*Venation*.—Type: Pinnate. Color: Venation color upper side: Near RHS Green 137D. Venation color under side: Near RHS Green 143D.

*Petiole*.—Length: Average 2 mm. Diameter: Average 2 mm. Color: Upper side: Near RHS Greyed-Purple N186A. Under side: Near RHS Greyed-Purple N186B.

FLOWER

Not observed.

REPRODUCTIVE ORGANS

Not observed.

OTHER CHARACTERISTICS

Disease/pest resistance: Neither resistance nor susceptibility to normal diseases and pests of *Ulmus* has been observed.

Drought tolerance: No tolerance for drought observed. *Ulmus crassifolia* can be moderately drought tolerant once established.

Temperature tolerance: USDA Zones 6 through 9.

Fruits/nuts: Not observed.

What is claimed is:

1. A new and distinct cultivar of *Ulmus crassifolia* tree named 'UCMTF' as herein illustrated and described.

* * * * *